United States Patent

Beck et al.

[11] 4,125,722
[45] Nov. 14, 1978

[54] PROCESS FOR THE PREPARATION OF TETRACHLOROPYRIMIDINE

[75] Inventors: Gunther Beck; Helmut Heitzer, both of Leverkusen, Germany

[73] Assignee: Bayer Aktiengesellschaft, Leverkusen, Germany

[21] Appl. No.: 842,976

[22] Filed: Oct. 17, 1977

[30] Foreign Application Priority Data

Oct. 20, 1976 [DE] Fed. Rep. of Germany ....... 2647313

[51] Int. Cl.$^2$ .......................................... C07D 239/24
[52] U.S. Cl. .................................................. 544/334
[58] Field of Search .................................... 260/251 R

[56] References Cited

U.S. PATENT DOCUMENTS

| | | | |
|---|---|---|---|
| 3,075,980 | 1/1963 | Benz | 260/251 R |
| 3,714,164 | 1/1973 | Steffan | 260/251 R |
| 3,997,554 | 12/1976 | Van Eyck et al. | 260/251 R |
| 4,026,892 | 5/1977 | Beck et al. | 260/251 R |

Primary Examiner—Nicholas S. Rizzo
Attorney, Agent, or Firm—Plumley and Tyner

[57] ABSTRACT

Process for the preparation of tetrachloropyrimidine, characterized in that compounds of the formula

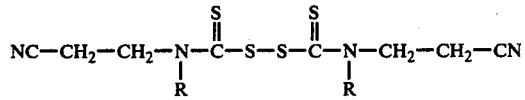

wherein
  R = a radical which can be split off under the reaction conditions, are reacted with chlorine or agents which release chlorine, preferably at temperatures from 0°–150° C and using more than 7 mols of chlorine, in particular using 11–13 mols of chlorine.

5 Claims, No Drawings

PROCESS FOR THE PREPARATION OF TETRACHLOROPYRIMIDINE

The present invention relates to a new process for the preparation of tetrachloropyrimidine.

The process is characterised in that N,N'-bis-(2-cyanoethyl)-thioperoxydicarboxylic acid diamides of the formula

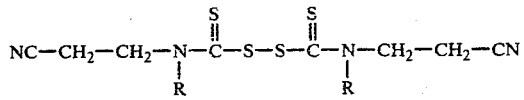

wherein
R denotes a radical which can be split off under the reaction conditions,
are treated with chlorine or an agent which releases chlorine, if appropriate mixed with an inert diluent. The reaction is carried out at temperatures from 0°–150° C. and in general with more than 7 mols of chlorine, preferably 11–13 mols of chlorine, and especially 13 mols of chlorine, per mol of (I). In a preferred embodiment, the chlorination is carried out at temperatures from about 40° C. to about 70° C. until the evolution of HCl has virtually ended and the mixture is then further heated to temperatures from 70° to 150° C, if appropriate with the further addition of chlorine or a chlorinating agent. A further preferred embodiment consists in carrying out the chlorination at temperatures from about 40° to 130° C.

Suitable radicals R which can be split off under the reaction conditions are, in particular, lower alkyl, preferably $C_1$-$C_4$-alkyl, such as methyl, ethyl, propyl or butyl, and furthermore, lower alkenyl, especially $C_2$-$C_4$-alkenyl, such as allyl, it being possible for these groups also to be substituted, for example by chlorine, $C_1$-$C_4$-alkoxy or optionally substituted phenyl.

Suitable radicals of this type are, for example, chloroethyl, methoxyethyl, benzyl, phenylethyl, chloropropyl, dichloropropyl and methoxypropyl. Methyl is particularly preferred.

In addition to chlorine, all the customary chlorinating agents which can split off chlorine under the reaction conditions are, of course, suitable.

Examples which may be mentioned are: sulphur dichloride, sulphuryl chloride and phosphorus pentachloride.

Only some of the starting compounds of the formula (I) are known. However, they can be easily prepared according to the instructions in the literature (for example Acta Chim. Acad. Sci. Hung. 51, 319 (1967)) by initially reacting, according to the following equation.

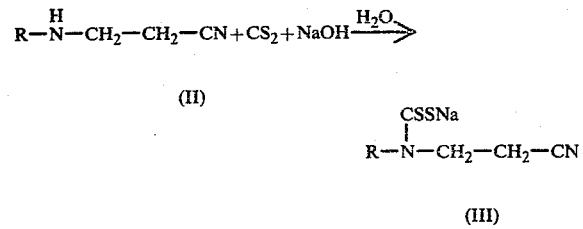

cyanoethylated amines (II), in which R has the meaning given above, with carbon disulphide in aqueous sodium hydroxide solution to give the dithiocarbamates of the formula (III), which are then converted, by oxidation, into the disulphides of the formula (I), for example using hydrogen peroxide in sulphuric acid according to the following equation:

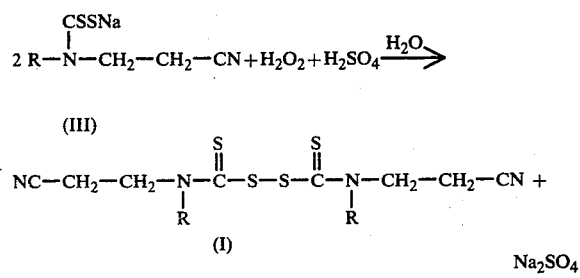

The cyanoethylated amines (II) are obtained, for example, according to the following equation

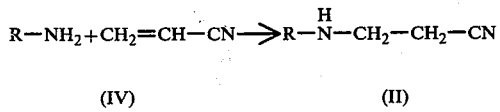

by subjecting primary amines (IV), in which R has the meaning given above, to an addition reaction with acrylonitrile. (Compare, for example, J. Am. Chem. Soc. 66, 725 (1944), J. Am. Chem. Soc. 68, 1217 (1946), J. Am. Chem. Soc. 78, 2573 (1956) and J. Heterocyclic Chem. 1, 260 (1964).

N,N'-bis-(2-cyanoethyl)-thioperoxydicarboxylic acid diamides of the formula (I) which are suitable for the process according to the invention are, for example: N,N'-bis-(2-cyanoethyl)-N,N'-dimethyl-thioperoxydicarboxylic acid diamide, N,N'-bis-(2-cyanoethyl)-N,N-diethyl-thioperoxydicarboxylic acid diamide, N,N'-bis-(2-cyanoethyl)-N,N'-bis-(2-chloroethyl)-thioperoxydicarboxylic acid diamide, N,N'-bis-(2-cyanoethyl)-N,N'-bis-(2-methoxyethyl)-thioperoxydicarboxylic acid diamide, N,N'-bis-(2-cyanoethyl)-N,N'-dipropyl-thioperoxydicarboxylic acid diamide, N,N'-bis-(2-cyanoethyl)-N,N'-diallyl-thioperoxydicarboxylic acid diamide, N,N'-bis-(2-cyanoethyl)-N,N'-bis-(3-methoxypropyl)-thioperoxydicarboxylic acid diamide, N,N'-bis-(2-cyanoethyl)-N,N'-bis-(2,3-dichloropropyl)-thioperoxydicarboxylic acid diamide, N,N'-bis-(2cyanoethyl)-N,N'-dibutylthioperoxydicarboxylic acid diamide, N,N'-bis-(2-cyanoethyl)-N,N'-dibenzyl-thioperoxydicarboxylic acid diamide and N,N'-bis-(2-cyanoethyl)-N,N'-diphenylethyl-thioperoxydicarboxylic acid diamide.

Diluents which are inert under the reaction conditions are all solvents which are stable towards chlorine, for example chlorinated aliphatic and aromatic hydrocarbons, such as methylene chloride, chloroform, carbon tetrachloride, 1,1,2,2-tetrachloroethane, tetrachloroethylene, 1,1,2,3,3-pentachloropropane, hexachlorocyclopentadiene, octachlorocyclopentene and 1,2,4-trichlorobenzene, chlorinated pyrimidines and phosphorus oxychloride. In general, 0.5 to 20, preferably 1 to 10, parts by volume of diluent are used per part by weight of (I).

In the case where the chlorinating agent is a liquid under the reaction conditions, such as, for example, sulphur dichloride or sulphuryl chloride, the additional use of an inert diluent can be omitted.

If chlorine is used as the chlorinating agent, the reaction initially proceeds strongly exothermically. Thus, it is appropriate — especially when larger batches are used — not to carry out the chlorination with an excess of chlorine until the exothermic reaction has subsided. After the strongly exothermic first chlorination phase has subsided, the chlorination is appropriately carried out with an excess of chlorine (recognisable by the greenish colour of the chlorination off-gas) in order to end the reaction as rapidly as possible. If other chlorinating agents are used, for example $SCl_2$, it can be appropriate to employ an excess from the beginning.

In detail, the process is carried out by initially mixing a N,N'-bis-(2-cyanoethyl)-thioperoxydicarboxylic acid diamide of the formula (I), especially N,N'-bis-(2-cyanoethyl)-N,N'-dimethyl-thioperoxydicarboxylic acid diamide or also, N,N'-bis-(2-cyanoethyl)-N,N'-diethyl-thioperoxydicarboxylic acid diamide, with one of the diluents mentioned, for example chloroform, at room temperature and then adding the chlorinating agent. External cooling and metering of the chlorinating agent are matched with one another so that the initially strongly exothermic reaction does not become too violent.

Chlorination is preferably carried out at about 40°-70° C. until the evolution of HCl has virtually ended.

If the chlorination is carried out in the absence of an inert diluent using a chlorinating agent which is liquid under the reaction conditions, such as, for example, sulphur dichloride, it is advisable initially to introduce the latter and to meter in the starting material (I) in portions at a temperature at which it reacts with the chlorinating agent as rapidly as possible, that is to say, for example, between 40 and 70° C., preferably 50° and 60° C.

A particularly favourable embodiment of the process consists in initially carrying out the chlorination at about 40°-70° C. until the evolution of HCl has virtually ended and then heating the mixture, without further addition of chlorine or a chlorinating agent, to temperatures up to about 100° C., and in particular appropriately until the evolution of HCl, which starts again, has virtually ended.

Tetrachloropyrimidine is suitable thus a reactive component for the preparation of reactive dyestuffs (compare, for example, Belgian Patent Specification No. 578,933).

EXAMPLE 1

636 g (2.0 mols) of N,N'-bis-(2-cyanoethyl)-N,N'-dimethyl-thioperoxydicarboxylic acid diamide are dissolved in about 2 liters of chloroform in a 4 liter 3-necked flask which is provided with a thermometer, gas inlet tube, stirrer and reflux condenser. A vigorous stream of chlorine (initially about 800 g/hour) is passed in, whilst stirring and cooling with ice to about 0°-5° C., whereby the internal temperature rises to 40°-45° C. in the course of about half an hour. After this first stage, which is the most strongly exothermic, has subsided, the stream of chlorine is reduced so that chlorine is always present in a slight excess (recognisable, for example, by the light green colour of the off-gas) and the external cooling is reduced to such an extent that the reaction temperature can rise to 50°-55° C. in the following 2 hours. The mixture is then subsequently heated for the first time, a reflux temperature of about 57° C. being reached after about 3.5 hours from the start of chlorination, whilst passing in a further slight excess of a stream of chlorine. The reflux condenser is now replaced by a distillation device and an internal temperature of 65° C. is thus reached after about 5.5 hours from the start of chlorination, whilst further chlorinating and gradually distilling off sulphur dichloride and chloroform.

Sulphur dichloride and chloroform are now distilled off until the internal temperature reaches about 90° C. and the residue, which contains tetrachloropyrimidine, is distilled under a waterpump vacuum, virtually all the constituents which can be distilled passing over at a boiling point$_{12}$ of 108°-110° C. 740 g of a tetrachloropyrimidine, which is 99% pure according to gas chromatography, are thus obtained. This corresponds to a pure yield of tetrachloropyrimidine of 84%.

EXAMPLE 2

45 g (0.141 mol) of N,N'-bis-(2-cyanoethyl)-N,N'-dimethyl-thioperoxydicarboxylic acid diamide are metered in small portions into 450 ml (about 7 mols) of sulphur dichloride at a temperature between about 45° and 55° C., with the exclusion of atmospheric moisture. The temperature is then gradually raised to about 65° C. and kept there until the evolution of gas has virtually ended. Thereafter, distillation is carried out under normal pressure until the internal temperature reaches about 100° C. and the residue is then fractionated under a waterpump vacuum. After a first running which essentially consists of disulphur dichloride, a distillate which passes over almost exclusively at a boiling point$_{12}$ of 108°-110° C. and which contains 53.5 g (corresponding to 87% of theory) of tetrachloropyrimidine is thus obtained.

EXAMPLE 3

In a solution of 20 g (57.8 mmols) of N,N'-bis-(2-cyanoethyl)-N,N'-diethyl-thioperoxydicarboxylic acid diamide (melting point 98° C; prepared according to Acta Chim. Acad. Sci. Hung. 51 319) in about 100 ml of chloroform is chlorinated, initially whilst cooling with ice and, after the first strongly exothermic phase has subsided, whilst warming and under reflux (about 56° C.) until virtually no further chlorine is absorbed. Sulphur dichloride and chloroform are then distilled off in a weak stream of chlorine until the sump temperature reaches about 80° C. The residue is distilled as described in the examples above. 23 g of an almost 99% pure tetrachloropyrimidine are thus obtained. Pure yield of tetrachloropyrimidine: 90% of theory.

We claim:

1. Process for the preparation of tetrachloropyrimidine, characterised in that compounds of the formula

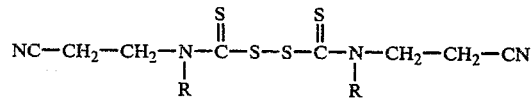

wherein
- R = $C_1$-$C_4$-alkyl, optionally substituted by chlorine, $C_1$-$C_4$-alkoxy or phenyl are reacted with a chlorinating agent selected from the group consisting of chlorine, sulfur dichloride, sulfuryl chloride and phosphorus pentachloride at temperatures from 0°-150° C. and using more than 7 mols of chlorinating agent.

2. Process according to claim 1, characterised in that the chlorination is carried out at temperatures from 40°-130° C.

3. Process according to claim 1, characterised in that the chlorination is carried out at about 40°–70° C. until the evolution of HCl has virtually ended and the mixture is then subsequently heated to temperatures of about 70°–150° C; if appropriate in the presence of chlorine.

4. Process according to claim 1 in which R is methyl.

5. Process according to claim 1 in which R is ethyl.

* * * * *

UNITED STATES PATENT AND TRADEMARK OFFICE
CERTIFICATE OF CORRECTION

PATENT NO. : 4,125,722
DATED : November 14, 1978
INVENTOR(S) : Gunther Beck, et al.

It is certified that error appears in the above–identified patent and that said Letters Patent are hereby corrected as shown below:

Column 4, line 38, insert --,-- after "51" and underscore.

Column 4, line 60, Claim 1, after "phenyl" insert ---; $C_2$-$C_4$-alkenyl, optionally substituted by chlorine; $C_1$-$C_4$-alkoxy or phenyl---.

Signed and Sealed this

Second Day of October 1979

[SEAL]

Attest:

RUTH C. MASON
Attesting Officer

LUTRELLE F. PARKER
Acting Commissioner of Patents and Trademarks